United States Patent [19]

Wielinger et al.

[11] Patent Number: 4,786,603
[45] Date of Patent: Nov. 22, 1988

[54] METHOD FOR SEPARATING PLASMA FROM BLOOD AND SILANIZED GLASS FIBRES THEREFOR

[75] Inventors: Hans Wielinger; Helmut Freitag, both of Weinheim, Fed. Rep. of Germany

[73] Assignee: Boehringer Mannheim GmbH, Mannheim, Fed. Rep. of Germany

[21] Appl. No.: 21,743

[22] Filed: Mar. 4, 1987

Related U.S. Application Data

[62] Division of Ser. No. 881,835, Jul. 3, 1986, abandoned.

[30] Foreign Application Priority Data

Jul. 4, 1985 [DE] Fed. Rep. of Germany ....... 3523969

[51] Int. Cl.[4] ..................... G01N 21/78; G01N 30/00; G01N 33/86
[52] U.S. Cl. ................................ 436/69; 210/500.24; 210/500.26; 210/508; 210/509; 422/55; 422/56; 428/391; 428/392; 428/401; 436/170; 436/178; 435/13
[58] Field of Search .................. 436/69, 170, 177, 148; 422/55-58; 210/508, 509, 679, 500.24, 500.26; 435/13; 428/391, 392, 375, 361, 401

[56] References Cited

U.S. PATENT DOCUMENTS

| | | | |
|---|---|---|---|
| 2,563,288 | 8/1951 | Steinmann | 428/391 |
| 2,683,097 | 7/1954 | Biefeld | 428/391 |
| 2,946,701 | 7/1960 | Plueddemann | 428/391 |
| 3,253,948 | 5/1966 | Tiede | 428/391 |
| 3,702,783 | 11/1972 | Hartlein | 428/391 |
| 3,791,933 | 2/1974 | Moyer et al. | 195/127 |
| 4,246,107 | 1/1981 | Takenaka et al. | 210/806 |
| 4,472,303 | 9/1984 | Tanihara . | |
| 4,477,575 | 10/1984 | Vogel et al. | 436/170 |

OTHER PUBLICATIONS

Ohlson et al., "High Performance Liquid Affinity Chromatography . . . ", *FEBS Letters* 93, 5-9 (1978).
Larsson et al., High-Performance Liquid Affinity . . . ", *Adv. Chromatography* 21, 48-55 (1978) [Excerpt.].

*Primary Examiner*—Barry S. Richman
*Assistant Examiner*—Robert J. Hill, Jr.
*Attorney, Agent, or Firm*—Felfe & Lynch

[57] ABSTRACT

Hydrophilic glass fibers which have bonded to their surfaces a layer of silane molecules of the formula

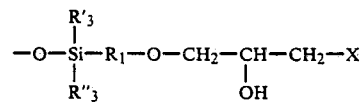

are useful for the separation of plasma from blood for haemostasiological testing. In the formula: the molecule is bonded at its end oxygen to a surface of a glass fibre; $R_1$ is $C_2$–$C_6$ alkylene; X is OH, $C_1$–$C_6$ alkoxy, having n carbon atoms and up to (n−1) OH groups in which n is 1–6, or an amino acid or peptide residue; and each of $R'_3$ and $R''_3$ is $C_1$–$C_6$ alkyl, an oxygen bridge to the silicon atom of another silane molecule or an oxygen bridge to the glass surface. The fibres have an average diameter of from 0.2 to 5 microns and a density of 0.1 to 0.5 g/cm$^3$.

14 Claims, 1 Drawing Sheet

METHOD FOR SEPARATING PLASMA FROM BLOOD AND SILANIZED GLASS FIBRES THEREFOR

This is a division of application Ser. No. 881,835 filed on July 3, 1986, now abandoned.

BACKGROUND OF THE INVENTION

The present invention is concerned with coagulation-neutral, hydrophilic glass fibres, a process for the production thereof and an agent for the separation of plasma from blood.

European patent specification No. 00 45 476 describes agents and processes for the separation of plasma or serum from whole blood which make it possible to determine component materials from whole blood in a simple way. According to this patent specification, the plasma can be separated from the erythrocytes by allowing whole blood to run through a layer of glass fibres with fibre diameters of less than 2.5μ, the glass fibres holding back the erythrocytes. The blood is preferably applied to one end of a rectangular glass fibre fleece, from whence the plasma is transported capillarily into the other region. There is then pressed onto the part of the fleece filled with plasma, a matrix (paper, absorbent film, etc.) containing the reagents needed for a detection reaction for the parameter to be determined via measurements of diffuse reflectivity.

This simple plasma obtaining and plasma transport system can be used for all clinical-chemically important parameters with the exception of parameters which are to be determined in the scope of the investigations of haemostasiological questions. It is known that coagulation analyses are carried out in synthetic resin vessels or glass vessels which are inactivated by a coating of silicone resin because untreated glass influences the coagulatability of blood or plasma. Thus, by activation, glass shortens the Prothrombin time of plasmas having coagulation factors which lie in the normal range. The Prothrombin time is prolonged in the case of low percentage plasmas by inactivation of coagulation factors. Glass inactivates, in particular, Factors V and IIa. Due to this inactivation and thus falsely prolonged Prothrombin time, the diagnostic use is destroyed because the ratios of the individual coagulation factors are displaced. The Prothrombin time value given as a percentage (Quick %) includes the fibrinogen concentration and the activity of Factors II, V, VII and X. A pool plasma from healthy donors is defined as 100% plasma and, by way of dilution with physiological saline, corresponding lower percentage plasmas are prepared. By means of this dilution series, a reference curve is produced on the basis of which the Prothrombin time values for patients' plasmas are determined.

However, the determination of the activated partial thromboplastin time (PTT) is also negatively influenced by the inactivation of Factors XII and XI. The detection of anti-thrombin III and heparin is considerably disturbed by an inactivation of thrombin by glass.

Therefore, it is an object of the present invention to modify the separation and transport systems according to European patent specification No. 00 45 476 so that they become coagulation-neutral without changing their separation and transport properties so that they can also be used for haemostasiological investigations.

A possible solution to the above problems is to use fibre materials made from synthetic resins. However, with regard to their separation behaviour towards the erythrocytes, these fibre materials do not have the desired properties and, in part, considerably influence the coagulatability of plasmas. It is also known that glasses can be superficially coated by siliconization with silicone resin emulsions to exclude the influencing of the coagulation factors thereby. However, this siliconization brings about, in the special case of the glass fibres, such a strong hydrophobing of the surface that wetting can no longer take place and thus the fibres completely lose their erythrocyte separation and plasma transport properties.

SUMMARY OF THE INVENTION

Surprisingly, we have found that glass fibre surfaces can be so chemically modified with certain silanes that they retain their hydrophilic properties, which are necessary, for example, for the absorbency of glass fibre fleeces, but lose their influence on the coagulation factors, i.e. become coagulation-neutral.

By means of the treatment of glass fibres with compounds of the following general formula (I), there are obtained, with intermediate splitting of the alkoxy groups to give hydroxyl groups and subsequent reaction of these hydroxyl groups with the reactive places of the glass fibre surface, glass fibres which have the above-described properties.

The compounds used for this purpose have the following general formula:

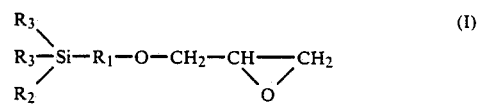

wherein $R_1$ is an alkylene radical containing 2 to 6 carbon atoms, $R_2$ is an alkoxy radical containing up to 6 carbon atoms and $R_3$ is an alkyl or alkoxy radical containing up to 6 carbon atoms.

DETAILED DISCLOSURE

Figure 1:
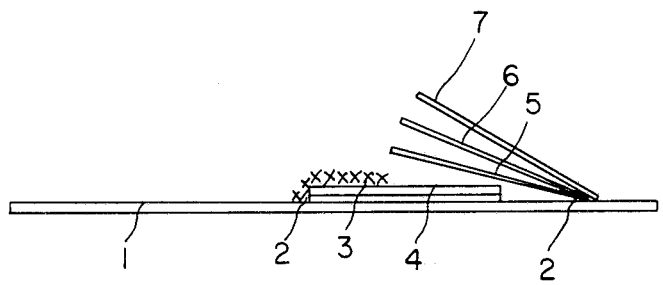
FIG. 1 illustrates the cross section of a test strip for determination of prothrombin, as described in Example 3.

The treatment of the glass fibres takes place in a known manner by using compounds of general formula (I) (FEBS Lett. 93, 5–6/1978) which are easily acid adjusted in aqueous solutions. In the case of this procedure, not only are reactive Si-OH groups formed, which react with the glass surface, but also the oxiran rings react to give diols. When using silanes with one alkoxy radical $R_2$, monomolecular layers are obtained. When using silanes with 2 or 3 alkoxy radicals, there are obtained, depending upon the reaction conditions, multilayer coatings (1–30 and normally 4–12 layers), since the silanes also react with one another by polycondensation.

An advantageous possibility is the coating of the glass surface with compounds of the general formula (I) in anhydrous organic solvents, optionally with catalysis by weak bases, and subsequent reaction of the oxiran rings to give diols by acid catalysis in aqueous solution (Advan. Chromatogr., 21, 48-53/1978). According to this process, there can be built up monomolecular layers or layers which have a thickness of a few silane molecules.

Furthermore, it is also possible to utilize the reactivity of the oxiran or of the diol group in order to attach further ligands thereon which keep the glass coagulation-neutral but change the degree of hydrophilia insofar as this appears necessary and the additional expense is justified. Strongly ionic ligands are thereby excluded since they influence the coagulation but a coupling of amino acids and peptides can be advantageous. An alcoholysis of the oxiran ring with a monohydroxy alcohol gives more hydrophobic glycol monoethers and with polyols gives hydrophilic polyol compounds.

The end product obtained has the following schematically illustrated structure:

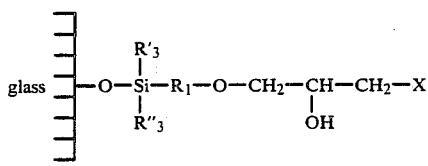

wherein $R_1$ is an alkylene radical containing 2 to 6 carbon atoms, X is a hydroxyl group, an alkoxy radical optionally substituted by one or more hydroxyl groups, preferably an alkoxy radical having n carbon atoms and up to (n−1) hydroxyl groups wherein n is 1 to 6, or an amino acid or peptide residue and $R'_3$ and $R''_3$ are either lower alkyl radicals or oxygen bridges to the silicon atoms of the neighboring group or to the glass surface.

Glasses/glass fibres modified in this way have a neutral behaviour with regard to the coagulation cascade.

The alkylene radicals $R_1$ can be straight-chained or branched radicals containing 2 to 6 carbon atoms, the silicon atom being separated from the ether oxygen by at least 2 carbon atoms. Ethylene and propylene radicals are preferred as alkylene radicals $R_1$.

The alkyl and alkoxy radicals $R_2$ and $R_3$ can be straight-chained and branched radicals containing up to 6 carbon atoms, methyl, ethyl, methoxy and ethoxy radicals being preferred, which are simple to prepare and to react. Insofar as X is an alkoxy radical, this also contains up to 6 carbon atoms, methoxy, ethoxy, propoxy, 2-hydroxyethyleneoxy and 2,4-dihydroxypropyleneoxy being the preferred radicals. The amino acid and peptide residues are preferably derived from the amino acids and peptides present in human serum, especially albumin, by means of which the coagulation cascade is not disturbed.

The glass fibres according to the present invention are converted according to conventional processes into fleeces which, as is described in the following Examples, can be employed in agents for the determination of coagulation parameters. The glass fibres used in the agent can have an average diameter of 0.2 to 5μ and preferably of 0.5 to 2.5μ and a density of 0.1 to 0.5 g./cm$^3$. However, they can also be used in the form of a short column for obtaining plasma according to European patent specification No. 00 45 476 and the plasma so obtained can then be used in conventional manner in coagulation tests. The fibres are thereby preferably layered in the column, the head of which is provided with means for the application of blood and the end of which is provided with means for the removal of plasma.

Further embodiments of the agent according to the present invention for the separation of plasma and for use in diagnostic agents for the determination of coagulation parameters can be produced analogously to the agents described in European patent specification No. 00 45 476, to which reference is hereby made. It is obvious that in such agents, not only the glass fibre layers according to the present invention but also all other parts coming into contact with the plasma must consist of coagulation-neutral materials, whereby, in particular, there are used appropriate synthetic resins known to the expert. In such agents, the glass fibre layer is preferably the uppermost layer of a multilayer diagnostic agent and is preferably in absorbent contact with a plasma transport layer which, in turn, is in absorbent contact with one or more reagent layers or can be brought into contact with these.

The following Examples are given for the purpose of illustrating the present invention:

EXAMPLE 1

Production of coagulation-neutral glass fibres

To 1 liter of water, which has been brought with an acid (e.g. hydrochloric acid or acetic acid) to a pH of 2.0–4.0 and preferably of 3.0, are added 5 to 50 g. and preferably 20 g. γ-glycidoxypropyltrimethoxysilane. For the splitting off of methanol and for the formation of Si—OH groups, the mixture is stirred until turbidity can no longer be seen. The reaction can be accelerated by increasing the temperature. A reaction time of 1 hour at 80° C. has proved to be especially useful. Into this solution are introduced 0.5 to 10 g. and preferably 2 to 7 g. of glass fibres. The mixture is further stirred for 1 to 4 hours and preferably for 1 hour, the silane thereby being bound to the glass surface and the oxiran ring being reacted to give a diol group. At higher temperatures, the reaction proceeds more quickly. The glass fibres are filtered off with suction and thoroughly washed with water. The glass fibres are slurried in 1 liter of water which has been adjusted with hydrochloric acid to a pH of 2.0 to 4.0 and preferably of 3.0, sheets with a surface weight of 20–200 g./m$^2$ being formed therefrom on a sheet former. The surface weight to be chosen depends upon the intended use of the fleece formed (see the Example describing this).

EXAMPLE 2

Testing of the glass fibres for coagulation neutrality 40 mg. Amounts of the glass fibres produced according to Example 1 are brought together with 300 μl. of pool plasma from healthy donors, as well as from patients treated with anticoagulants, and incubated for 1 minute at 37° C., whereafter the plasmas are separated by centrifuging. Before and after the treatment with glass, the plasmas are investigated for the Prothrombin time. The following clotting test can be used:

The coagulation cascade is initiated with calcium chloride and thromboplastin and a hook is drawn through the sample, the time being measured up to the formation of fibrin threads. A photometric test can also be employed for the determination of the Prothrombin time. (Becher, U. et al., Neue Aspekte in der Gegerinnungsdiagnostik, F. K. Schattauer Verlag, Stuttgart-New York (1984), pages 17–30).

Furthermore, the influence of thrombin (Factor IIa) is tested as follows. 300 μl. of a solution of thrombin in water containing about 3 U/ml. is brought together with glass in the above-described way. In the case of all experiments in which the glass has been modified according to the process of the present invention, no dfferences in the coagulation behaviour of plasmas occur before and after the treatment with modified glass. The thrombin activity (thrombin is completely inactivated by untreated glass) also remains unchanged.

The activity determination of the thrombin is carried out with Tos-Gly-Pro-Arg-p-nitroaniline as substrate. For this purpose, 2 ml. of Tris/HCl buffer (2.00 mmol/l.; pH 8.1) are incubated with 50 μl. thrombin solution at 25° C. for 3 minutes and then the reaction is started with 100 μl. of 3.8 mmol/l. substrate and the kinetics monitored.

EXAMPLE 3

Determination of the Prothrombin time

Preparation of the test

Reagent matrix

A paper with a surface absorbency of 60 to 70 ml./m² is impregnated with an aqueous solution of the following composition:
hepes: 250 mmol/l. (buffer)
Tos-Gly-Pro-Arg-p-phenylenediamine: 1 mmol/l. (substrate)
N-(4-fluorophenyl)-N-methylaminomethane-phosphonic acid: 30 mmol/l. (coupler)
rabbit brain thromboplastin: 1.2 g./l.

This solution is adjusted to pH 7.3 with aqueous sodium hydroxide solution.

After the drying, strips of 15 mm. breadth are cut from the impregnated paper.

Oxidation matrix

A nylon net with filament thickness about 40 μm. and a mesh size about 60 μm. (Type NY 20 HC Super of the firm Züricher Beuteltuchfabrik, Switzerland) is impregnated with an aqueous solution of 50 mmol potassium ferricyanide/l. and 50 mmol calcium chloride/l. After drying, 15 mm. wide strips are cut from the impregnated net.

Test construction

On a 100 mm. wide polystyrene foil are laid the glass fibre fleece according to the present invention with a surface weight of 50 to 60 g./m² in a width of 15 mm. and fixed with a nylon net with a filament thickness of 140 μm. and a mesh width of 250 μm. which is laid thereover and stuck on the end (see FIG. 1). On the free end of the glass fibre fleece, the oxidation and reagent matrices are laid over one another, covered with a 200μ thick transparent polycarbonate foil of 15 mm. width and firmly stuck (see FIG. 1). The bands so produced are cut up into 6 mm. wide strips.

FIG. 1 of the accompanying drawings shows the construction of the test strip. In this FIG. 1:
1. polystyrene carrier foil
2. adhesive
3. nylon net
4. glass fibre fleece according to the present invention
5. oxidation matrix
6. reagent matrix
7. polycarbonate covering foil.

Determination of the Prothrombin time

Comparison between test strips which have been produced with glass fibres according to the present invention and non-silanized glass fibres.

On to the nylon net with which the glass fibre fleece is fixed are pipetted 35 μl. of a citrate blood dilution series (haemocrit about 40%) of 100%, 50%, 33%, 25%, 12.5% blood in physiological saline solution. The erythrocytes are retained in the separation part. The test strips are then warmed to 37° C. and the colour formation monitored according to the time with a remission photometer. It is thereby observed that, with the glass fibres according to the present invention, substantially higher signals are obtained than with untreated glass fibres. When using silanized glass fibres, as Prothrombin time there can be taken the time within which a remission decrease of 10% remission is passed through. In contradistinction thereto, when using untreated glass fibres, there can only be used the times within which a change of 4% remission takes place. The deviations in the case of tests with the glass fibres according to the present invention are also markedly smaller since the glass does not exert a disturbing influencing on the course of the coagulation cascade. The differences are illustrated in the following Table (the Prothrombin time being indicated in Quick %).

TABLE

| Quick % | test with glass fibre fleeces according to the present invention time in sec. for a remission decrease of 10% | test with non-coated glass fleeces time in sec. for a remission decrease of 4% | photometric test with citrate plasma time in sec. for a remission decrease of 0.1 U |
|---|---|---|---|
| 100% | 36.2 | 27.5 | 33.2 |
| 50% | 44.7 | 48.8 | 45.8 |
| 33% | 53.2 | 71.8 | 57.8 |
| 25% | 61.0 | 94.4 | 67.0 |
| 12.5% | 95.1 | 200.0 | 116.0 |

From the above Table, it can be seen that, as is known of coagulation analyses by means of clotting tests, an activation by glass takes place in the case of plasmas from healthy donors (100% plasma), whereas low percentage plasmas are clearly inactivated.

Figure 2:
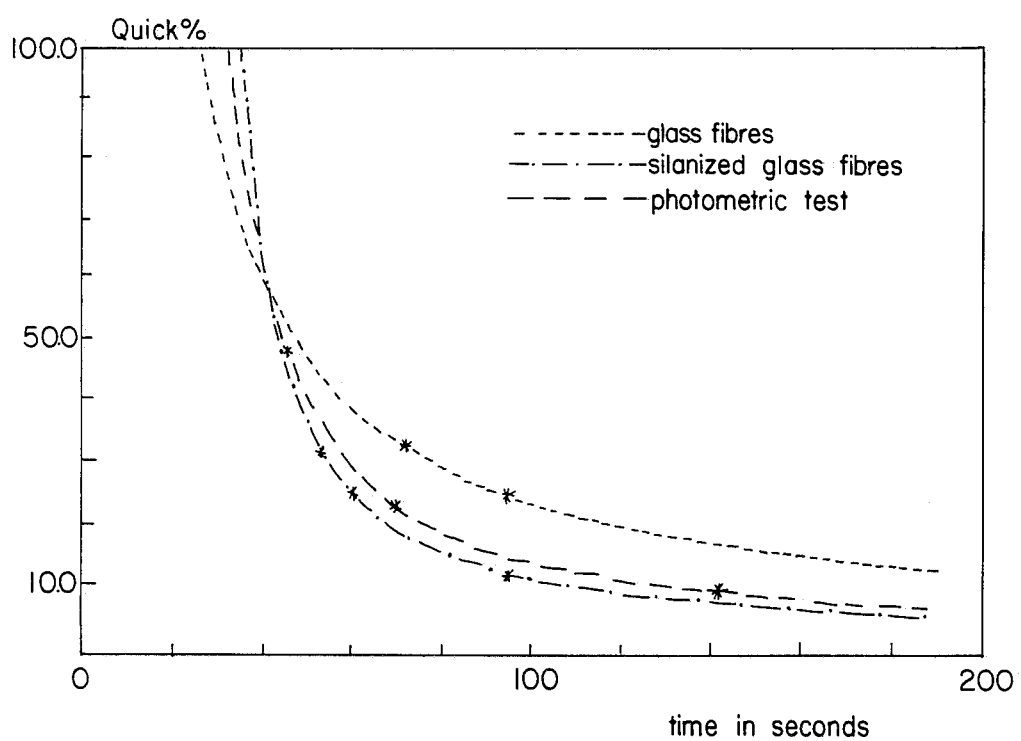
FIG. 2 shows reference curves for the measurement for Quick percent as described in Example 3 with glass fibers, silanized glass fibers and by a photometric test.

Furthermore, a reference curve which is obtained with a test construction with the glass fibres according to the present invention is very similar to that of the photometric Quick test (see FIG. 2 of the accompanying drawings).

What is claimed is:

1. An agent for separating plasma from blood for haemostasiological tests which comprises a layer of glass fibres having bonded to their surfaces a layer of silane molecules of the formula

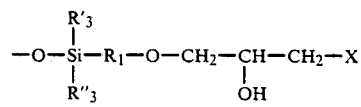

wherein
each molecule is bonded at its end oxygen to a surface of a glass fibre in the layer of glass fibres,
R₁ is C₂-C₆ alkylene, X is hydroxyl, $C_1$-$C_6$ alkoxy, an alkoxy radical having n carbon atoms and up to (n−1) hydroxyl groups in which n is an integer from 1 to 6, or an amino acid or peptide residue; and each of $R'_3$ and $R''_3$ is $C_1$-$C_6$ alkyl, an oxygen bridge to the silicon atom of another silane molecule, or an oxygen bridge to a glass surface,
said fibres having an average diameter of from 0.2 to 5μ and said glass fiber layer having density of 0.1 to 0.5 g./cm³.

2. The agent of claim 1, wherein the glass fibres have an average diameter of 0.5 to 2.5μ.

3. The agent of claim 1 wherein the fibres are layered in a column having a head which is provided with means for applying blood and an end which is provided with means for removing plasma.

4. The agent according to claim 1, wherein $R_1$ is ethylene or propylene.

5. A multi-layer diagnostic device for detecting blood coagulation parameters, which comprises an uppermost layer the agent of claim 1 wherein the glass fibre layer consists of a glass fibre paper or fleece.

6. The diagnostic device of claim 5, wherein the glass fibre layer is the uppermost layer of said device.

7. The diagnostic device of claim 5, wherein the glass fiber layer is in absorbent contact with a plasma transport layer which, in turn, is in absorbent contact with one or more reagent layers or can be brought into contact therewith.

8. A method for separating plasma from blood which comprises passing whole blood through an agent comprising a layer of glass fibres having bonded to their surfaces a layer of silane molecules of the formula

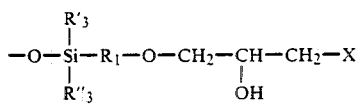

wherein
each molecule is bonded at its end oxygen to a surface of a glass fibre in the layer of glass fibres,
$R_1$ is $C_2$-$C_6$ alkylene,
X is hydroxyl, $C_1$-$C_6$ alkoxy, an alkoxy radical having n carbon atoms and up to (n−1) hydroxyl groups in which n is an integer from 1 to 6, or an amino acid or peptide residue; and
each of $R'_3$ and $R''_3$ is $C_1$-$C_6$ alkyl, an oxygen bridge to the silicon atom of another silane molecule, or an oxygen bridge to a glass surface, said fibres having an average diameter of from 0.2 to 5μ and said glass fibre layer having a density of 0.1 to 0.5 g./cm³.

9. The method according to claim 8, in which the glass fibres have an average diameter of from 0.5 to 2.5μ.

10. The method according to claim 8, wherein $R_1$ is ethylene or propylene.

11. The method according to claim 8, in which the fibres are layered in a column having a head which is provided with means for applying blood and an end which is provided means for removing plasma.

12. The method according to claim 8, wherein the glass fibre layer consists of a glass fibre paper or fleece and is part of a multi-layer diagnostic device for detecting coagulation parameters which has an uppermost layer.

13. The method according to claim 12, wherein the glass fibre layer is the uppermost layer of said diagnostic device.

14. The method according to claim 12, wherein the glass fibre layer is in absorbent contact with a plasma transport layer which, in turn, is in absorbent contact with one or more reagent layers or can be bought into contact therewith.

* * * * *

UNITED STATES PATENT AND TRADEMARK OFFICE
CERTIFICATE OF CORRECTION

PATENT NO. : 4,786,603

DATED : November 22, 1988

INVENTOR(S) : Hans Wielinger et al.

It is certified that error appears in the above-identified patent and that said Letters Patent is hereby corrected as shown below:

Column 7, line 27, "layer the agent" should read

-- layer and the agent --.

Signed and Sealed this

Twenty-third Day of May, 1989

Attest:

DONALD J. QUIGG

*Attesting Officer*      *Commissioner of Patents and Trademarks*